United States Patent [19]
Wolvek et al.

[11] Patent Number: 5,716,373
[45] Date of Patent: Feb. 10, 1998

[54] SUPPORT MEMBER FOR REDUCED DIAMETER BALLOON CATHETER, AND INTRA-AORTIC BALLOON CATHETER USING THE SAME

[75] Inventors: Sidney Wolvek, Brooklyn, N.Y.; Helio M. Ribeiro, Newark; Boris Leschinsky, Waldwick, both of N.J.

[73] Assignee: Datascope Investment Corp., Montvale, N.J.

[21] Appl. No.: 662,154

[22] Filed: Jun. 12, 1996

Related U.S. Application Data

[63] Continuation-in-part of Ser. No. 503,921, Jul. 19, 1995, abandoned.

[51] Int. Cl.⁶ ................................ A61M 29/00
[52] U.S. Cl. ................ 606/194; 606/191; 606/192
[58] Field of Search ................ 606/191, 192, 606/194

[56] References Cited

U.S. PATENT DOCUMENTS

| | | |
|---|---|---|
| 4,261,339 | 4/1981 | Hanson et al. |
| 5,042,985 | 8/1991 | Elliot et al. ............. 606/192 |
| 5,159,937 | 11/1992 | Tremulis ............. 606/194 |

OTHER PUBLICATIONS

"Webster's Ninth New Collegiate Dictionary", Merriam–Webster Inc. (1987), copyright pp. 942 and 1205.

*Primary Examiner*—Michael Buiz
*Assistant Examiner*—Daphna Shai
*Attorney, Agent, or Firm*—Fitzpatrick, Cella, Harper & Scinto

[57] ABSTRACT

A balloon catheter assembly in which the catheter tube terminates at the entrance to the balloon chamber and in which a thin support member connects the distal end of the catheter tube to the tip at the distal end of the balloon chamber. A connecting anchor is provided at the distal end of the catheter tube. The connecting anchor has a skirt portion that is connected to the catheter tube. The support member is attached to the skirt portion.

28 Claims, 4 Drawing Sheets

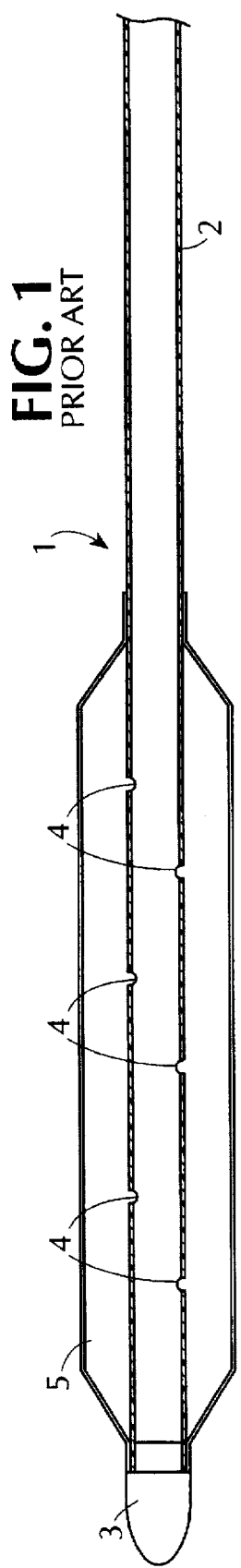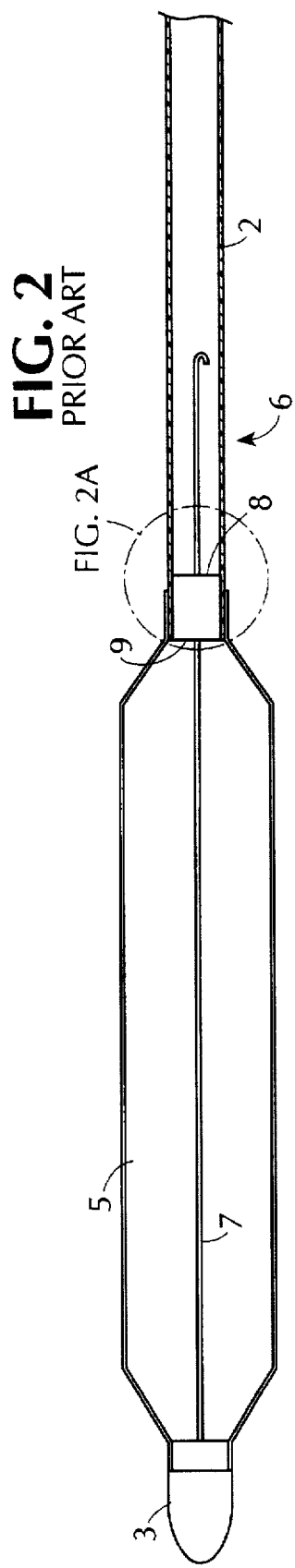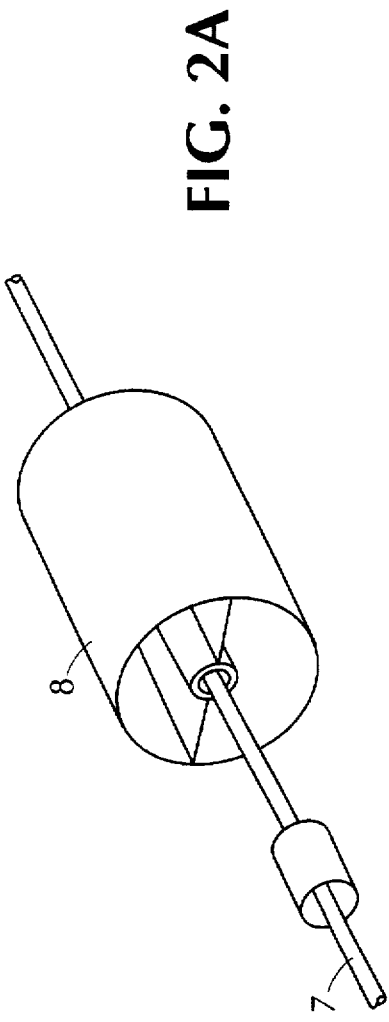

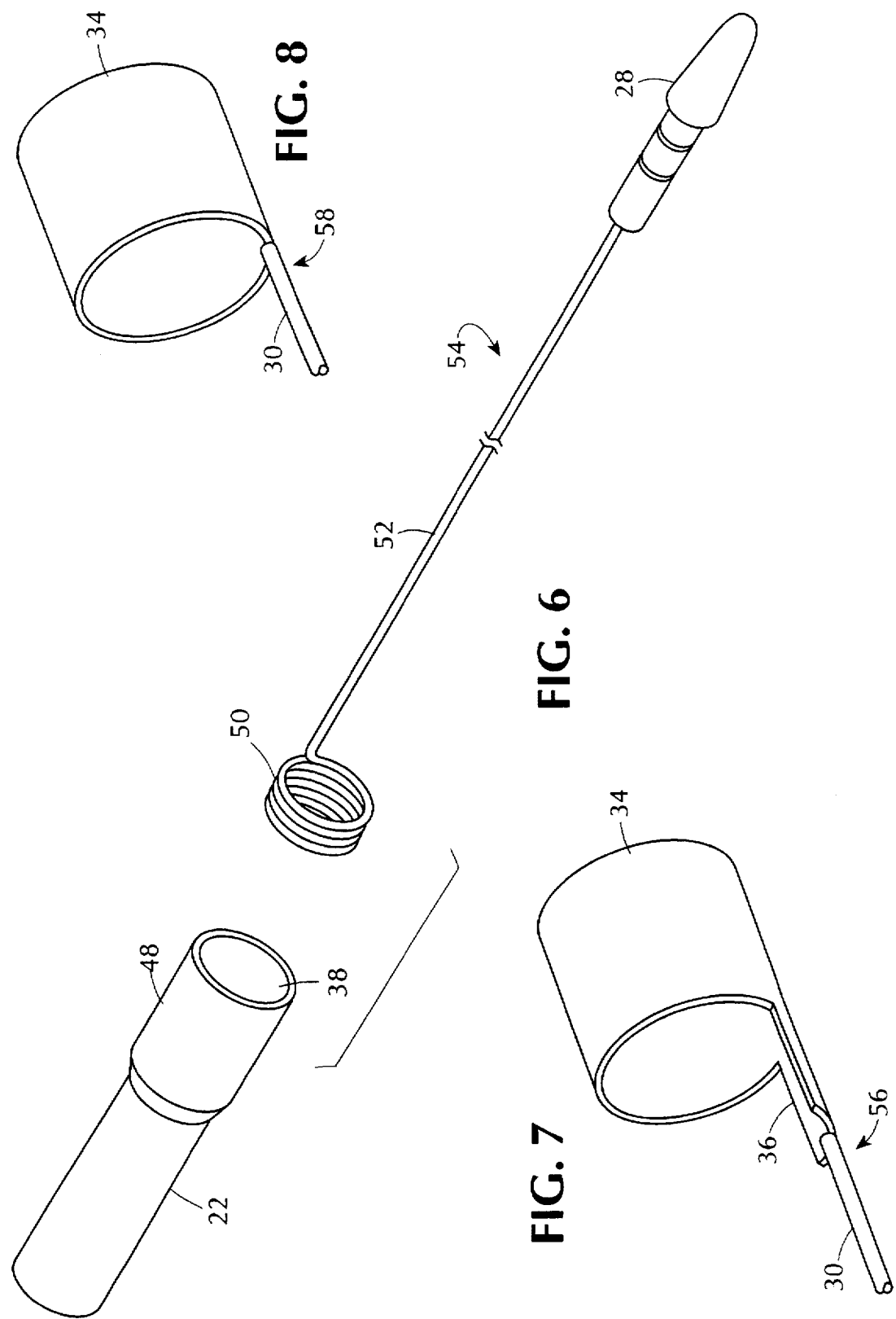

5,716,373

SUPPORT MEMBER FOR REDUCED DIAMETER BALLOON CATHETER, AND INTRA-AORTIC BALLOON CATHETER USING THE SAME

CROSS-REFERENCE TO RELATED APPLICATION

This application is a continuation-in-part of U.S. patent application Ser. No. 08/503,921, filed on Jul. 19, 1995, now abandoned.

BACKGROUND OF THE INVENTION

1. Field of the Invention

This invention relates generally to cardiac support equipment, and more particularly, to intra-aortic balloon pumping devices in which a working fluid is used to selectively inflate and deflate the intra-aortic balloon.

2. Background

Intra-aortic balloon pumping ("IABP") often referred to simply as "balloon pumping" or "counterpulsation", began in the late 1960s. As initially practiced, it necessitated a surgical cut-down procedure whereby a vascular surgeon would first cut through the skin and the subcutaneous tissue to expose the femoral artery. The surgeon would then cut through the wall of the artery and then suture a graft to the artery. With that complete, the intra-aortic balloon ("IAB") catheter would be fed through the graft, into the artery and up through the arterial system to the descending thoracic aorta. Once the IAB was properly positioned, the graft would be tied tightly around the catheter tube to prevent loss of blood from the artery. Counterpulsation could then begin without blocking blood flow to the affected leg.

In the second half of the 1970s, one of the present applicants, together with a co-worker, invented a new kind of IAB catheter (for which U.S. Pat. No. 4,261,339 issued) which permitted percutaneous insertion. Percutaneous insertion offers numerous advantages over the surgical cut-down procedure; it is much quicker, causes less trauma, does not require surgeons or a surgical environment (it can be done by invasive cardiologists in the cardiac catheterization laboratory or elsewhere), presents fewer risks of infection and enables much more rapid recovery. As a result, following introduction of the first PERCOR® IAB catheter in about late 1978 by the assignee of the present application, percutaneous insertion quickly became the method of choice and remains so to this time.

Although percutaneous IAB catheters have supplanted the older "surgical" catheters for almost all adult applications, the same cannot be said for pediatric uses. Unfortunately, because of the need to use very small balloons and balloon catheters, until now percutaneous IAB catheters have been unavailable for use in very small children. The present invention was designed primarily to overcome the impediments to percutaneous insertion of IAB catheters into infants. Likewise, this invention is suitable for use in situations where it is preferable to employ a reduced-diameter balloon catheter, for example, where a patient's circulatory system is such as to make the use of a conventional, large-size balloon undesirable.

DESCRIPTION OF THE RELATED ART

IAB catheters are used, for example, to reduce the burden on a still-beating human heart and to force blood to flow to the systemic arteries, for example, and to the coronary arteries, which are not receiving an adequate blood supply.

Percutaneous IAB catheters typically consist of a tip at the distal end, a sausage-shaped intra-aortic balloon ("IAB") attached at one end to the tip, balloon support means, a catheter tube attached to the other end of the balloon, and a fitting attached at the proximal end of the catheter tube. The fitting, catheter tube, and balloon are in fluid communication so that forcing gas through the fitting causes the balloon to inflate and removing gas through the fitting causes the balloon to deflate.

Adult-sized IAB catheters can be positioned in a patient's body using minimally-invasive catheterization procedures (i.e. percutaneously), rather than surgery. Typically, a sheath is inserted into a puncture wound in the groin and the furled IAB is inserted into the patient's femoral artery via the sheath, and is advanced until it is disposed within the patient's descending thoracic aorta. Now, the heart can be assisted by inflating and deflating the IAB in counterpulsation to the heart beat.

Over the years since introduction of the PERCOR®catheter, efforts have been made to reduce the diameter of the catheter tube. Since the catheter tube passes through and remains resident in the patient's arterial system, it is important that there be as much clearance as possible around that catheter for healthy blood flow to the distal leg. If too large a catheter is used, this may interfere with proper blood circulation past the catheter. If, however, too narrow a catheter is used, it becomes more difficult to shuttle gas through the catheter to inflate and deflate the balloon in time with the heart rate.

Because of the small size of an infant's arteries, a pediatric IAB catheter must be much smaller than an adult-sized catheter, preferably 7 Fr or smaller. In addition to having small arteries, infants also tend to have heart rates which are much more rapid than those of adults. Thus, although a pediatric IAB catheter must be smaller than one for an adult, it must also be able to shuttle gas back and forth at a more rapid rate. One of the difficulties in designing a pediatric IAB derives from this need to use a small-sized catheter. As the catheter size becomes smaller, frictional forces become much greater and the rapid movement of gas therethrough becomes much more difficult.

It is therefore particularly important in a pediatric IAB catheter to minimize impediments to gas flow. In prior art IAB catheters, the structures that enabled them to be inserted percutaneously, increased the resistance to gas flow to an extent that, although tolerable in an adult catheter, was not acceptable in a pediatric catheter. The present invention is directed primarily to overcoming this drawback of the prior art and permitting pediatric IAB catheters to be inserted percutaneously.

This invention is equally-applicable in those instances where it is preferable to use a reduced-diameter IAB balloon, rather than conventional, large-size devices.

The balloon membrane of an IAB has essentially no rigidity and is not self supporting. Therefore, in order to permit insertion through the arterial system, and use once properly positioned in the aorta, structure must be provided to prevent the membrane from folding back upon the catheter tube proximal to the balloon chamber. In the "surgical" catheters 1 (see FIG. 1) this was not a problem since the catheter tube 2 extended all the way to the tip 3. The support member for the balloon was the catheter tube itself. To permit gas to be pumped into and out of the IAB, holes 4 were provided in that portion of the catheter tube that was inside the balloon chamber 5.

With the advent of the PERCOR® percutaneous catheter 6 (see FIG. 2), the catheter tube 2 terminated immediately upon entry into the balloon chamber 5. Support for the balloon membrane was then provided by a short support wire 7 that ran from collar 8 inside the distal end 9 of the catheter tube, through the balloon chamber, to the tip 3.

In a subsequent design for a percutaneous catheter 11 (FIG. 3), the support wire 12 was extended so that it ran all the way from the tip 3, into and through the balloon chamber 5, and through the entire length of the catheter tube 2, into the fitting 10.

In both these versions of the percutaneous IAB catheters, the support member within the balloon chamber was a thin rod or wire. Because this support member was so thin, it enabled the balloon membrane to be twisted or wrapped or furled to a diameter which was as small as or smaller than that of the catheter tube to which it was attached so that the balloon catheter could be inserted through the smallest possible introducer sheath, thereby offering minimal obstruction to blood flow.

Unfortunately, as the diameter of the catheter tube was reduced in size, for example, to pediatric size, the structures shown in FIGS. 2 and 3 caused so much resistance to the flow of gas that pumping of a reduced-size/pediatric balloon became impractical. In the design shown in FIG. 2, the support collar 8 (see FIG. 2A) inside the distal end of catheter tube 2 was the primary cause of this resistance. In the design of FIG. 3, although support collar 8 had been removed, the full length support wire not only reduced the size of the useable lumen, but also produced frictional resistance to the flow of gas.

SUMMARY OF THE INVENTION

The present invention is directed primarily to an IAB catheter having a small diameter catheter tube and a small balloon chamber wherein the balloon tip is connected to the catheter tube by a narrow support rod. The design of the subject invention overcomes the problems associated with the prior art. It does this by employing only a short support member (even shorter in length than that depicted in FIG. 2) and attaching it to the catheter tube in such fashion as not significantly to restrict the flow of gas into and out of the balloon chamber.

BRIEF DESCRIPTION OF THE DRAWINGS

FIG. 1 is a schematic depiction of a prior art surgical IAB catheter.

FIG. 2 is a schematic depiction of a prior art percutaneous IAB catheter.

FIG. 2A is a perspective view of a portion of the IAB catheter shown in FIG. 2.

FIG. 6 is a perspective view of an alternative embodiment of a connecting anchor and support member according to the present invention.

FIG. 7 is a perspective view of a second alternative embodiment of a connecting anchor.

FIG. 8 is a perspective view of a third alternative embodiment of a connecting anchor.

DESCRIPTION OF THE PREFERRED EMBODIMENTS

The present invention is intended to improve the performance of intra-aortic balloon catheters. Briefly, one utilizing the present invention can obtain these benefits because of the manner in which the support member is connected to the catheter tube.

Figure 4:
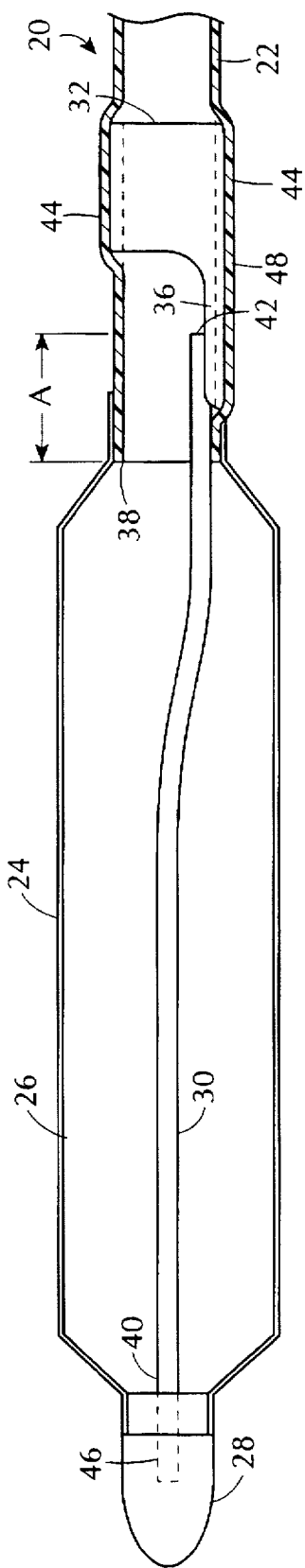
FIG. 4 is a schematic depiction of the distal end of an IAB catheter embodying the present invention.

The distal end of an IAB catheter embodying the present invention is depicted in FIG. 4. Catheter 20 is comprised of a catheter tube 22, a balloon membrane 24 defining a balloon chamber 26, a tip 28, a support member 30 and connecting anchor 32. The connecting anchor 32 is comprised of a ring or skirt portion 34 and a tang 36. Connecting anchor 32 is fixedly attached to catheter tube 22 adjacent the distal end 38 thereof. The skirt portion 34 of connecting anchor 32 is made of thin walled metal tubing such as hypotubing and is preferably connected within the distal end 48 of catheter tube 22 by swaging or dilating the distal end 48 to receive anchor 32. The distal end 48 is then swaged closed to its original dimension, thereby entrapping anchor 32.

Support member 30, preferably in the form of a thin wire or rod, is attached at its distal end 40 to tip 28 and at its proximal end 42 to tang 36 of connecting anchor 32. Support member 30 does not intrude into the diameter of skirt 34 so as not to impede the flow of inflating gas. In the preferred embodiment, support member 30 is fixedly attached to both tip 28 and anchor 32. Alternatively, rod 30 may be rotatably attached to tip 28.

Preferably, anchor 32 and support rod or wire 30 are made of stainless steel and can be attached by conventional means, for example, by silver soldering or, preferably, by spot welding, or by laser welding.

Although not critical, tip 28, which may be made of stainless steel, is laser welded or is silver soldered onto the distal end 40 of support wire 30 and may be covered with a layer of polyurethane or some other biocompatible material.

Membrane 24 and catheter tube 22 are made of conventional materials, preferably polyurethane. In the preferred configuration, the inside diameter of ring portion 34 of anchor 32 is approximately the same as the nominal inside diameter of catheter tube 22. Ring portion 34 is force fit into the distal end 48 of catheter tube 22 so as to distend tube 22 in region 44 thereby presenting the working fluid with a substantially constant cross-section therethrough.

Anchor 32 is inserted sufficiently far into catheter tube 22 so that tang 36 does not protrude beyond the distal tip 38. Anchor 32 can be attached to catheter tube 22 by conventional means for example, by heat shrinking catheter tube 22, by use of adhesive, such as cyanoacrylate adhesive, or preferably by use of both these means.

Although inserting anchor 32 into catheter tube 22 so that tang 36 does not protrude means that for a very short distance A, there will be a slight reduction in the cross section of the lumen presented to the working fluid, it is not believed that this will significantly impede fluid flow.

As noted above, anchor 32 is preferably formed from hypotubing having an inside and outside diameter equal to that of ring portion 34. If formed from hypotubing, tang 36 will have an arcuate shape to cradle support wire 30 and facilitate attachment between the two components.

A suitable reduced-size/pediatric IAB catheter according to the instant invention could have a polyurethane membrane 24 defining a balloon chamber 26 of 5 cc attached to a 5.5 Fr. polyurethane catheter tube. Such an IAB catheter would typically have a 0.017Δ by 6" long support wire. The skirt portion 34 of anchor 32 would be formed of thin walled hypotubing having an outside diameter of 0.058Δ and an inside diameter of 0.050.Δ The 5.5 Fr catheter tube into which it would be force fit has an inside diameter of 0.048Δ. The axial length of skirt portion 34 of anchor 32 would be about 0.150Δ and the axial length of tang 36 would be 0.10Δ.

An alternative embodiment of the connecting anchor and support member is depicted in FIG. 6. In this embodiment, the connecting anchor 54 is comprised of a coil, 50 preferably of flattened wire, and the support member 52 is simply a continuation of the coil wire which has not been formed into a coil. The coil of anchor 54 provides strain relief for support member 52.

Figure 3:
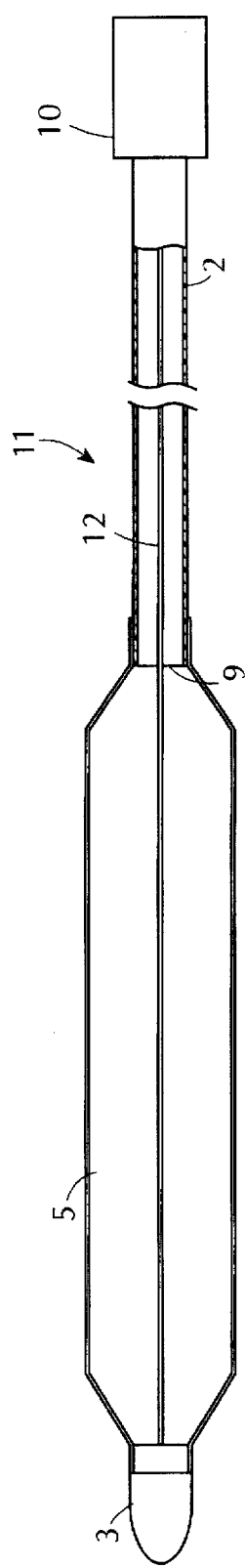
FIG. 3 is a schematic depiction of another form of prior art percutaneous IAB catheter.
Figure 5:
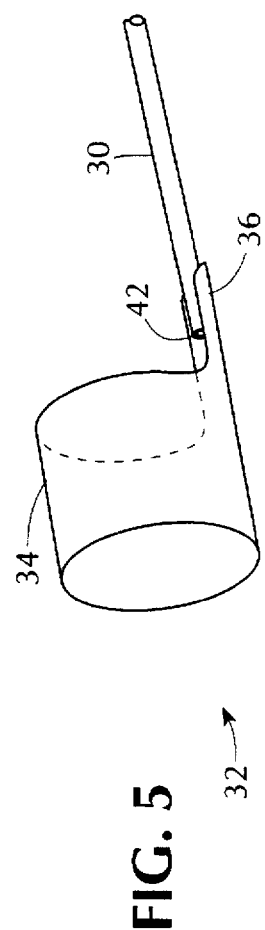
FIG. 5 is a perspective view of the connecting anchor of the IAB catheter shown in FIG. 4.

A second alternative embodiment of the connecting anchor is depicted in FIG. 7. The anchor of this embodiment is very similar to the one of FIG. 5 except that in the FIG. 7 embodiment, the support member 30 does not overlap tang 36 but rather is butt welded 56 to the edge of the distal tip of the tang.

Yet a third embodiment of the connecting anchor is depicted in FIG. 8. In this embodiment, the tang has been eliminated entirely. Instead, the proximal tip of support member 30 is butt welded 58 directly to skirt 34, which forms the entire connecting anchor. Support member 30 may be flattened at the weld point 60 to further reduce restriction to flow through skirt 34.

Figure 9:
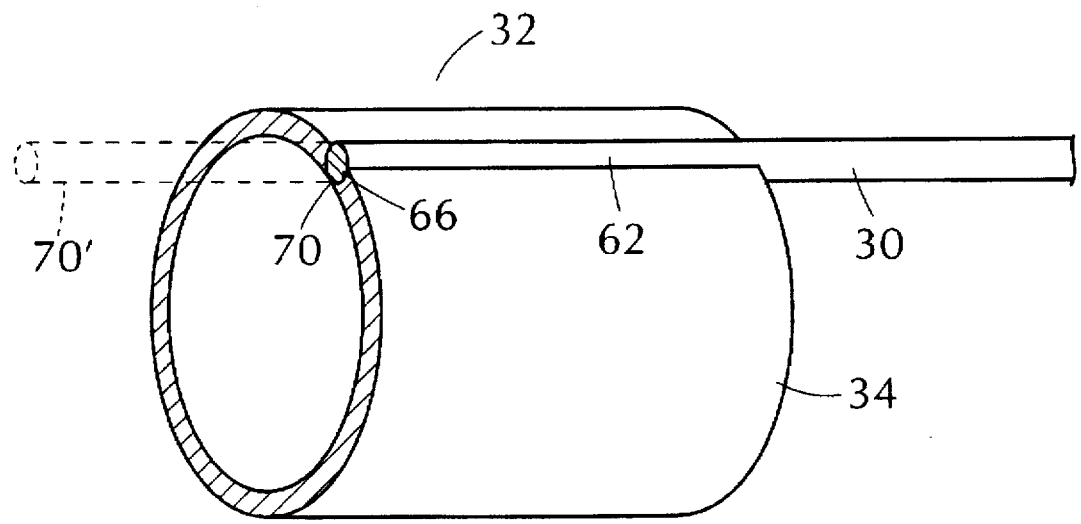
FIG. 9 is a perspective view of a fourth alternative embodiment of a connecting anchor.
Figure 10:
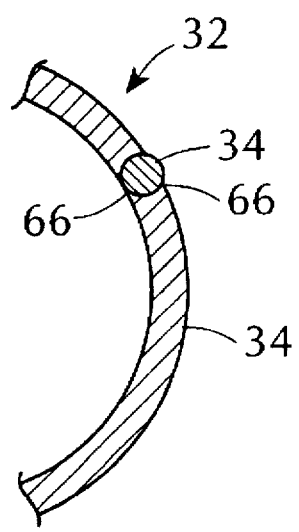
FIG. 10 is a cross-sectional view of the connector anchor shown in FIG. 9, as seen along line 10—10.

A fourth and particularly preferred embodiment of this invention is shown in FIGS. 9 and 10. In this embodiment, the connecting anchor 32 is formed by providing a cylindrical skirt 34, which has a slot 62 cut or otherwise formed therein. Support member 30 is then fitted into the slot 62 so that at least a portion of one end 64 of the support member rests inside the slot. The support member is joined to the connecting anchor 32 using any suitable attachment technique, such as those previously discussed, and is preferably laser-welded.

FIG. 10 is a cross-sectional view of the assembly shown in FIG. 9, and depicts the support member 30 held within the slot 62 in the connecting anchor 32. Weld material 66 fills at least some of the space between the support member and adjacent skirt material.

While the slot 62 in connecting anchor 32 is shown in FIG. 9 as extending from the distal face to the proximal face of the connecting anchor 32, it will be appreciated that the slot could run from the distal face to an intermediate part of the connecting anchor 322. Likewise, while the slot is shown as being parallel to the collar's axis, the slot could be provided at any other suitable angle, for example, at 45° to the collar axis. Such a slot would have a spiral shape, since it would pass across the curvature of the collar. The support member would be suitably configured to fit into that slot and still have the proper orientation inside the balloon chamber 26.

Although as shown in FIG. 9 the proximal end 70 of the support member 30 terminates at the proximal end of the connecting anchor 32, that end of the support member could also be extended for any desirable length beyond the connecting anchor and into the catheter lumen toward the user, as shown in phantom outline at 70'.

While designed primarily for use in a pediatric IAB catheter, the present invention is not intended to be so limited, and can be used whenever a small-size IAB balloon is to be preferred. Typically, balloons for pediatric IAB use range in size from about 2.5 cc to about 20 cc.

While the subject matter of this invention has been described in connection with several specific embodiments, it should be understood that numerous modifications could be made by persons of skill in this art without departing from the inventive concept described herein. Accordingly, the above description is intended to be merely illustrative and not limiting. The scope of the invention claimed should be understood as including all those alternatives, variants, modifications and equivalents which the above specification would readily suggest or which would readily occur or be apparent to one skilled in the art upon reading the above.

What we claim is:

1. A balloon catheter assembly comprising:

a tip;

a balloon membrane defining a balloon chamber;

a catheter tube having a distal end and a lumen therein, said catheter tube lumen being in fluid communication with said balloon chamber;

a support member having a distal end and a proximal end;

a connecting anchor having a generally circular lumen which is substantially unobstructed, said connecting anchor being attached adjacent said distal end of said catheter tube, said connecting anchor having a skirt portion to which said proximal end of said support member is attached, said skirt portion being dimensioned and disposed such that said skirt and a portion of said support member attached thereto do not substantially block said lumen, said distal end of said support member being attached to said tip.

2. A balloon catheter assembly according to claim 1 further comprising a tang extending distally from said skirt portion and wherein said support member is attached at its proximal end to said tang.

3. A balloon catheter assembly according to claim 2, wherein said tang is entirely within said lumen of said catheter tube.

4. A balloon catheter assembly according to claim 2 wherein a portion of said catheter tube adjacent the distal end thereof is dilated and wherein said skirt portion of said anchor is resident in said dilated portion of said catheter tube.

5. A balloon catheter assembly according to claim 2 wherein a portion of said catheter tube adjacent the distal end thereof is dilated and wherein said skirt portion and said tang of said anchor are resident in said dilated portion of said catheter tube.

6. A balloon catheter assembly according to claim 1 wherein said skirt portion has an inside diameter of about the same size as the inside diameter of said catheter tube lumen.

7. A balloon catheter assembly according to claim 2 wherein said proximal end of said support member is distal of said skirt portion of said connecting anchor.

8. A balloon catheter assembly according to claim 1 wherein said support member is rotatably connected at its distal end to said tip.

9. An intra-aortic balloon catheter assembly according to claim 1.

10. A balloon catheter assembly comprising:

a tip;

a balloon membrane defining a balloon chamber;

a catheter tube having a distal end and a lumen therein, said catheter tube lumen being in fluid communication with said balloon chamber;

a connecting anchor having a proximal end and a distal end, said connecting anchor having a generally circular lumen which is substantially unobstructed, said connecting anchor being of about the same size as the lumen in said catheter tube; and a support member having a distal end and a proximal end, said proximal end being attached to said connecting anchor at said distal end of said anchor, said proximal end being attached to said connecting anchor in a manner such that said generally circular lumen is not substantially blocked by a portion of said support member attached thereto, and said distal end of said support member being attached to said tip.

11. A balloon catheter assembly according to claim 10 wherein a portion of said catheter tube adjacent the distal end thereof is dilated and wherein at least a portion of said connecting anchor is resident within said dilated portion of said catheter tube.

12. A balloon catheter assembly according to claim 10 wherein said connecting anchor is in the form of a coil.

13. A balloon catheter assembly according to claim 11 wherein said connecting anchor is in the form of a coil.

14. A balloon catheter assembly according to claim 12 wherein said support member is attached to the distal end of said coil.

15. A balloon catheter assembly according to claim 13 wherein said support member is attached to the distal end of said coil.

16. A balloon catheter assembly according to claim 14 wherein said support member is a straight continuation portion of said coil.

17. A balloon catheter assembly according to claim 15 wherein said support member is a straight continuation portion of said coil.

18. A balloon catheter assembly according to claim 10 wherein said connecting anchor is comprised of hypotubing.

19. A balloon catheter assembly according to claim 18 wherein said connecting anchor further comprises a tang extending distally from said hypotubing and wherein said support member is attached to said tang.

20. A balloon catheter assembly comprising:

a tip;

a balloon membrane defining a balloon chamber;

a catheter tube having a distal end and a lumen therein, said catheter tube lumen being in fluid communication with said balloon chamber;

a support member having a distal end and a proximal end;

a collar-shaped connecting anchor having a generally circular lumen which is substantially unobstructed, said connecting anchor being attached adjacent to said distal end of said catheter tube, said connecting anchor having a slot running at least partially therethrough, wherein said distal end of said support member is attached to said tip and said proximal end of said support member is disposed within said slot and is attached to said connecting anchor in a manner such that said generally circular lumen is not substantially blocked by a portion of said support member attached to said connecting anchor.

21. A balloon catheter assembly according to claim 20, wherein said slot is parallel to an axis of said connecting anchor.

22. A balloon catheter assembly according to claim 20 wherein a portion of said catheter tube adjacent the distal end thereof is dilated and wherein said connecting anchor is resident in said dilated portion of said catheter tube.

23. A balloon catheter assembly according to claim 20 wherein a portion of said catheter tube adjacent the distal end thereof is dilated and wherein said connecting anchor is resident in said dilated portion of said catheter tube.

24. A balloon catheter assembly according to claim 20 wherein said connecting anchor has an inside diameter of about the same size as the inside diameter of said catheter tube lumen.

25. A balloon catheter assembly according to claim 20 wherein said support member is rotatably connected at its distal end to said tip.

26. A balloon catheter assembly according to claim 20, wherein said slot extends from a proximal end of said connecting anchor to a distal end of said connecting anchor.

27. A balloon catheter assembly according to claim 26, wherein said support member extends past said proximal end of said connecting anchor away from said tip.

28. An intra-aortic balloon catheter assembly according to claim 20.

* * * * *